(12) United States Patent
Anderson et al.

(10) Patent No.: US 8,333,963 B2
(45) Date of Patent: Dec. 18, 2012

(54) METHOD OF INHIBITING OSTEOCLAST ACTIVITY

(75) Inventors: Dirk M Anderson, Port Townsend, WA (US); Laurent J Galibert, Prevessin Moens (FR)

(73) Assignee: Immunex Corporation, Thousand Oaks, CA (US)

( * ) Notice: Subject to any disclaimer, the term of this patent is extended or adjusted under 35 U.S.C. 154(b) by 0 days.

(21) Appl. No.: 12/850,368

(22) Filed: Aug. 4, 2010

(65) Prior Publication Data

US 2011/0086033 A1     Apr. 14, 2011

Related U.S. Application Data

(60) Continuation of application No. 12/137,397, filed on Jun. 11, 2008, now Pat. No. 7,790,684, and a continuation of application No. 09/705,985, and a continuation of application No. 11/881,911, filed on Jul. 30, 2007, which is a division of application No. 10/405,878, filed on Apr. 1, 2003, now Pat. No. 7,262,274, which is a continuation of application No. 09/871,291, filed on May 30, 2001, now Pat. No. 6,562,948, which is a division of application No. 09/577,800, filed on May 24, 2000, now Pat. No. 6,479,635, which is a continuation of application No. 09/466,496, filed on Dec. 17, 1999, now Pat. No. 6,528,482, which is a continuation of application No. 08/996,139, filed on Dec. 22, 1997, now Pat. No. 6,017,729.

(60) Provisional application No. 60/110,836, filed on Dec. 3, 1998, provisional application No. 60/085,487, filed on May 14, 1998, provisional application No. 60/064,671, filed on Oct. 14, 1997, provisional application No. 60/077,181, filed on Mar. 7, 1997.

(51) Int. Cl.
*A61K 39/395* (2006.01)
*C07K 16/28* (2006.01)
*C07K 16/22* (2006.01)

(52) U.S. Cl. ............... 424/130.1; 424/143.1; 424/145.1; 530/387.1; 530/388.22; 530/388.24; 530/389.2

(58) Field of Classification Search .................. None
See application file for complete search history.

(56) References Cited

U.S. PATENT DOCUMENTS

| | | | |
|---|---|---|---|
| 5,116,952 A * | 5/1992 | Martin et al. ............... 530/399 |
| 5,843,678 A | 12/1998 | Boyle | |
| 6,015,938 A | 1/2000 | Boyle et al. | |
| 6,017,729 A | 1/2000 | Anderson et al. | |
| 6,087,555 A | 7/2000 | Dunstan et al. | |
| 6,121,002 A * | 9/2000 | Robins ............... 435/7.1 |
| 6,150,090 A | 11/2000 | Baltimore et al. | |
| 6,242,213 B1 | 6/2001 | Anderson | |
| 6,242,586 B1 | 6/2001 | Gorman et al. | |
| 6,271,349 B1 | 8/2001 | Dougall | |
| 6,284,485 B1 | 9/2001 | Boyle et al. | |
| 6,284,728 B1 | 9/2001 | Boyle et al. | |
| 6,284,740 B1 | 9/2001 | Boyle et al. | |
| 6,288,032 B1 | 9/2001 | Boyle et al. | |
| 6,316,408 B1 | 11/2001 | Boyle | |
| 6,369,027 B1 | 4/2002 | Boyle et al. | |
| 6,410,516 B1 | 6/2002 | Baltimore et al. | |
| 6,419,929 B1 | 7/2002 | Anderson | |
| 6,479,635 B1 | 11/2002 | Anderson et al. | |
| 6,525,180 B1 | 2/2003 | Gorman et al. | |
| 6,528,482 B1 | 3/2003 | Anderson et al. | |
| 6,537,763 B2 | 3/2003 | Dougall et al. | |
| 6,562,948 B2 | 5/2003 | Anderson | |
| 6,649,164 B2 | 11/2003 | Maraskovsky | |
| 6,740,522 B2 | 5/2004 | Anderson | |
| 6,838,262 B1 | 1/2005 | Anderson | |
| 7,063,841 B2 | 6/2006 | Gorman et al. | |
| 7,097,834 B1 | 8/2006 | Boyle | |
| 7,125,686 B1 * | 10/2006 | Goto et al. ............... 435/69.1 |
| 7,262,274 B2 | 8/2007 | Anderson et al. | |
| 7,364,736 B2 | 4/2008 | Boyle et al. | |
| 7,411,050 B2 | 8/2008 | Anderson | |
| 7,718,776 B2 | 5/2010 | Boyle et al. | |
| 7,744,886 B2 | 6/2010 | Anderson | |
| 7,932,375 B2 | 4/2011 | Anderson | |
| 8,153,775 B2 | 4/2012 | Anderson | |
| 2003/0100488 A1 | 5/2003 | Boyle | |
| 2003/0103978 A1 | 6/2003 | Deshpande et al. | |
| 2003/0104485 A1 | 6/2003 | Boyle | |
| 2003/0144480 A1 | 7/2003 | Gorman et al. | |
| 2005/0003400 A1 | 1/2005 | Boyle | |

(Continued)

FOREIGN PATENT DOCUMENTS

EP     0816380     1/1998

(Continued)

OTHER PUBLICATIONS

Anderson et al., "A homologue of the TNF receptor and its ligand enhance T-cell growth and dendritic-cell function," *Nature* 390:175-179, 1997.

Baker, Stacey J. and Reddy, E. Premkumar, "Transducers of life and death: TNF receptor superfamily and associated proteins," *Oncogene*, 12(1):1-9, 1996.

Bluemke et al., "Skeletal complications of radiation therapy," Radiographs 1994; 14:111-121.

*Boyle v. Gorman and Mattson*, Board of Patent Appeals and Interferences, Interference No. 104,336 (Paper No. 39), Jun. 28, 2000.

Castro et al., "15 years experience with helium ion radiotherapy for uveal melanoma," Int J Radiat Oncol Biol Phys 1997; 39(5):989-996 (abstract only).

(Continued)

*Primary Examiner* — David Romeo
(74) *Attorney, Agent, or Firm* — Scott L. Ausenhus

(57) ABSTRACT

Methods for inhibiting osteoclastogenesis by administering a soluble RANK polypeptide are disclosed. Such methods can be used to treat a variety of different cancers, including bone cancer, multiple myeloma, melanoma, breast cancer, squamous cell carcinoma, lung cancer, prostate cancer, hematologic cancers, head and neck cancer and renal cancer.

7 Claims, No Drawings

U.S. PATENT DOCUMENTS

| | | |
|---|---|---|
| 2005/0089522 A1 | 4/2005 | Anderson |
| 2006/0246064 A1 | 11/2006 | Boyle |
| 2008/0009014 A1 | 1/2008 | Anderson |
| 2009/0004196 A1 | 1/2009 | Anderson et al. |
| 2012/0034690 A1 | 2/2012 | Anderson |

FOREIGN PATENT DOCUMENTS

| | | |
|---|---|---|
| EP | 0873998 | 10/1998 |
| EP | 0874045 A1 | 10/1998 |
| EP | 0911342 | 4/1999 |
| EP | 0955372 A2 | 10/1999 |
| WO | WO 93/08207 | 4/1993 |
| WO | WO 94/10308 | 11/1994 |
| WO | WO 95/33051 | 7/1995 |
| WO | WO 96/34095 | 10/1996 |
| WO | WO 96/40918 | 12/1996 |
| WO | WO 97/23614 | 3/1997 |
| WO | WO 98/07840 A1 | 2/1998 |
| WO | WO 98/25958 | 6/1998 |
| WO | WO 98/28423 | 7/1998 |
| WO | WO 98/28424 A2 | 7/1998 |
| WO | WO 98/46751 | 10/1998 |
| WO | WO 98/49305 A1 | 11/1998 |
| WO | WO 98/54201 | 12/1998 |
| WO | WO 99/19468 A1 | 4/1999 |
| WO | WO 99/29865 | 6/1999 |
| WO | WO 99/53942 A1 | 10/1999 |
| WO | WO 99/58674 A2 | 11/1999 |
| WO | WO 99/65449 | 12/1999 |
| WO | WO 99/65495 | 12/1999 |
| WO | WO 01/03719 A2 | 1/2001 |
| WO | WO 01/17543 A2 | 3/2001 |
| WO | WO 01/18203 A1 | 3/2001 |
| WO | WO 01/23549 | 5/2001 |
| WO | WO 01/62932 | 8/2001 |
| WO | WO 02/15846 A2 | 2/2002 |
| WO | WO 03/002713 A2 | 9/2003 |
| WO | WO 03/086289 | 10/2004 |

OTHER PUBLICATIONS

Darnay et al., *J. Biol. Chem.* 273(32):20551-20555; 1998.

DiBiase et al., "Palliative irradiation for focally symptomatic metastatic renal cell carcinoma: support for escalation based on a biological model," J Urol 1997; 158(3 Pt 1):746-749 (abstract only).

El-Shirbiny et al., "Technetium-99m-MIBI versus fluorine-18-FDG in diffuse multiple myeloma," J Nuclear Med 1997; 38:1208-1210.

Fisher et al., "Reanalysis and results after 12 years of follow-up in a randomized clinical trial comparing total mastectomy . . . with or without irradiation in the treatment of breast cancer." N Engl J Med 333:1456-1461 (1995).

Forman et al.,"The experience with neutron irradiation in locally advanced adenocarcinoma of the prostate," Semin Urol Oncol 1997; 4:239-243 (abstract only).

Fu, Radiation therapy with 5-fluorouracil in head and neck cancer, Semin Radiat Oncol 1997; 7(4):274-282 (abstract only).

Fuller, K., et al., "TRANCE is necessary and sufficient for osteoblast-mediated activation of bone resorportion in osteoclasts." J. Exp. Med., 188:997-1001 (1998).

Galibert et al., "The involvement of multiple tumor necrosis factor receptor (TNFR)-associated factors in the signaling mechanisms of receptor activator of NF-κB, a member of the TNFR superfamily," J. Biol. Chem. 273(51):34120-34127, 1998.

Guise, Theresa A. and Mundy, Gregory R., "Cancer and bone," Endocrine Reviews 19(1):18-54,1998.

Kodaira et al., "Cloning and characterization of the gene encoding mouse osteoclast differentiation factor," Gene 230:121-127, 1999.

Kwon et al., "cDNA sequences of two inducible T-cell genes," Proc. Natl. Acad. Sci. USA 86:1963, 1989.

Lacey et al., "Osteoprotegerin ligand is a cytokine that regulates osteoclast differentiation and activation," Cell, 93:165-175, 1998.

Mayer e al., "Postoperative radiotherapy in radically resected non-small cell lung cancer." CHEST 112:954-959 (1997).

Monfardini et al., "Recombinant antibodies in bioactive peptide design," JBC 1995; 270:6628-6638.

Nakagawa et al., "RANK is the essential signaling receptor for osteoclast differentiation factor in osteoclastogenesis," Biochem. And Biophys. Res. Comm. 253:395-400, 1998.

Reddi, A. H. "Bone morphogenesis and modeling: soluble signals sculpt osteosomes in the solid state," Cell, 89:159-161 (1997).

Roodman, G. David, "Advances in bone biology: the osteoclast," Endocr Rev. 17(4):308-332, 1996.

Simonet et al., "Osteoprotegerin: A novel secreted protein involved in the regulation of bone density," Cell 89:309-319, 1997.

Smith, C. et al., "A receptor for tumor necrosis factor defines an unusual family of cellular and viral proteins," Sci. 248:1019-1022, 1990.

Suda et al., "Modulation of osteoclast differentiation by local factors," Bone 17(2):87S-91S; 1995.

Suda et al., "Modulation of osteoclast differentiation," Endocr Rev. 13:66-80, 1992.

Suda et al., "Modulation of osteoclast differentiation: update 1995," in Endocr Rev. Monographs,4(1):266-270; 1995.

Takada et al., "A simple method to assess osteoclast-mediated bone resorption using unfractionated bone cells," Bone Miner., 17:347-359 (1992).

Takahashi N et al., "A new member of tumor necrosis factor ligand family, ODF/OPGL/TRANCE/RANKL, regulates osteoclast differentiation and function," Biochem Biophys Res Commun 1999; 256:449-455.

Tsuda et al., "Isolation of a novel cytokine from human fibroblasts that specifically inhibits osteoclastogenesis," Biochem. Biophys. Res. Commun., 234(1):137-142 (1997).

Tsukii K et al., "Osteoclast differentiation factor mediates an essential signal for bone resorption induced by 1α,25-dihydroxyvitamin D3, prostaglandin E2, or parathyroid hormone in the microenvironment of bone," Biochem Biophys Res Commun 1998; 246:337-341.

Wiley, SR et al., "Identification and characterization of a new member of the TNF family that induces apoptosis," Immunity 1995; 3(6):673-682.

Williams (Ed.), Current Problems in Cancer 1997; pp. 133-169.

Wong et al., "The TRAF family of signal transducers mediates NF-κB activation by the TRANCE receptor," J. Biol. Chem. 273(43):28355-28359, 1998.

Wong et al., "TRANCE (Tumor necrosis factor [TNF]-related activation-induced cytokine), a new TNF family member predominantly expressed in T cells, is a dendritic cell-specific survival factor," J. Exp. Med. 186(12):2075-2080, 1997.

Wong et al., "TRANCE is a novel ligand of the tumor necrosis factor receptor family that activates c-Jun N-terminal kinase in T cells," J. of Biological Chemistry 272(40):25190-25194, 1997.

Xing et al., "Mechanisms by which NF-κB regulates osteoclast numbers," Abstract ASBMR Meeting, U of TX Health Science Center, 1998.

Yasuda et al., "Osteoclast differentiation factor is a ligand for osteoprotegerin/osteoclastogenesis-inhibitory factor and is identical to TRANCE/RANKL," Proc. Natl. Acad. Sci. 95:3597-3602, 1998.

Yun et al., "OPG/FDCR-1, a TNF receptor family member, is expressed in lymphoid cells and is up-regulated by ligating CD401," J. Immunol. 161:6113-6121, 1998.

Read, "Experimental therapies for sepsis directed against tumour necrosis factor," J Antimicrob Chemother 41(Suppl. A):65-69, 1998.

Oyajobi et al., "Therapeutic efficacy of a soluble receptor activator of nuclear factor κB IgG Fc fusion protein in suppressing bone resorption and hypercalcemia in a model of humoral hypercalcemia of malignancy," Cancer Res 61:2572-2578, 2001.

Roodman, "Osteoclast function in Paget's Disease and multiple myeloma," Bone 17(2)(Suppl):57S-61S, 1995.

Body et al., "A phase I study of AMGN-0007, a recombinant osteoprotegerin construct, in patients with multiple myeloma or breast carcinoma related bone metastases," Cancer 2003; 97(3 Suppl):887-892.

Croucher et al., "Osteoprotegerin inhibits the development of osteolytic bone disease in multiple myeloma," Blood 2001; 98:3534-3540.

Lacey et al., "Osteoprotegerin ligand modulates murine osteoclast survival in vitro and in vivo," Am J Pathol 2000; 157(2):435-448.

Lacey et al., "Bench to bedside: elucidation of the OPG-RANK-RANKL pathway and the development of denosumab," Nat Rev Drug Discov 2012; 11:401-419.

Vanderkerken et al., "Recombinant osteoprotegerin decreases tumor burden and increases survival in a murine model of multiple myeloma," Cancer Res 2003; 63:287-289.

Vitovski et al., "Investigating the interaction between osteoprotegerin and receptor activator of NF-κβ or tumor necrosis factor-related apoptosis-inducing ligand," J Biol Chem 2007; 282:31601-31609.

* cited by examiner

SEQUENCE LISTING

```
<160> NUMBER OF SEQ ID NOS: 8

<210> SEQ ID NO 1
<211> LENGTH: 3136
<212> TYPE: DNA
<213> ORGANISM: Homo sapiens
<220> FEATURE:
<221> NAME/KEY: CDS
<222> LOCATION: (39)..(1889)

<400> SEQUENCE: 1
ccgctgaggc cgcggcgccc gccagcctgt cccgcgcc atg gcc ccg cgc gcc cgg         56
                                          Met Ala Pro Arg Ala Arg
                                          1               5 cgg cgc cgc ccg ctg ttc gcg ctg ctg ctc tgc gcg ctc ctc gcc               104
Arg Arg Arg Pro Leu Phe Ala Leu Leu Leu Cys Ala Leu Leu Ala
            10                  15                  20 cgg ctg cag gtg gct ttg cag atc gct cct cca tgt acc agt gag aag          152
Arg Leu Gln Val Ala Leu Gln Ile Ala Pro Pro Cys Thr Ser Glu Lys
        25                  30                  35 cat tat gag cat ctg gga cgg tgc tgt aac aaa tgt gaa cca gga aag          200
His Tyr Glu His Leu Gly Arg Cys Cys Asn Lys Cys Glu Pro Gly Lys
    40                  45                  50 tac atg tct tct aaa tgc act act acc tct gac agt gta tgt ctg ccc          248
Tyr Met Ser Ser Lys Cys Thr Thr Thr Ser Asp Ser Val Cys Leu Pro
55                  60                  65                  70 tgt ggc ccg gat gaa tac ttg gat agc tgg aat gaa gaa gat aaa tgc          296
Cys Gly Pro Asp Glu Tyr Leu Asp Ser Trp Asn Glu Glu Asp Lys Cys
                    75                  80                  85 ttg ctg cat aaa gtt tgt gat aca ggc aag gcc ctg gtg gcc gtg gtc          344
```

```
                Leu Leu His Lys Val Cys Asp Thr Gly Lys Ala Leu Val Ala Val Val
                         90                  95                 100 gcc ggc aac agc acg acc ccc cgg cgc tgc gcg tgc acg gct ggg tac        392
Ala Gly Asn Ser Thr Thr Pro Arg Arg Cys Ala Cys Thr Ala Gly Tyr
            105                 110                 115 cac tgg agc cag gac tgc gag tgc tgc cgc cgc aac acc gag tgc gcg        440
His Trp Ser Gln Asp Cys Glu Cys Cys Arg Arg Asn Thr Glu Cys Ala
        120                 125                 130 ccg ggc ctg ggc gcc cag cac ccg ttg cag ctc aac aag gac aca gtg        488
Pro Gly Leu Gly Ala Gln His Pro Leu Gln Leu Asn Lys Asp Thr Val
135                 140                 145                 150 tgc aaa cct tgc ctt gca ggc tac ttc tct gat gcc ttt tcc tcc acg        536
Cys Lys Pro Cys Leu Ala Gly Tyr Phe Ser Asp Ala Phe Ser Ser Thr
                155                 160                 165 gac aaa tgc aga ccc tgg acc aac tgt acc ttc ctt gga aag aga gta        584
Asp Lys Cys Arg Pro Trp Thr Asn Cys Thr Phe Leu Gly Lys Arg Val
            170                 175                 180 gaa cat cat ggg aca gag aaa tcc gat gcg gtt tgc agt tct tct ctg        632
Glu His His Gly Thr Glu Lys Ser Asp Ala Val Cys Ser Ser Ser Leu
        185                 190                 195 cca gct aga aaa cca cca aat gaa ccc cat gtt tac ttg ccc ggt tta        680
Pro Ala Arg Lys Pro Pro Asn Glu Pro His Val Tyr Leu Pro Gly Leu
200                 205                 210 ata att ctg ctt ctc ttc gcg tct gtg gcc ctg gtg gct gcc atc atc        728
Ile Ile Leu Leu Leu Phe Ala Ser Val Ala Leu Val Ala Ala Ile Ile
215                 220                 225                 230 ttt ggc gtt tgc tat agg aaa aaa ggg aaa gca ctc aca gct aat ttg        776
Phe Gly Val Cys Tyr Arg Lys Lys Gly Lys Ala Leu Thr Ala Asn Leu
                235                 240                 245 tgg cac tgg atc aat gag gct tgt ggc cgc cta agt gga gat aag gag        824
Trp His Trp Ile Asn Glu Ala Cys Gly Arg Leu Ser Gly Asp Lys Glu
            250                 255                 260 tcc tca ggt gac agt tgt gtc agt aca cac acg gca aac ttt ggt cag        872
Ser Ser Gly Asp Ser Cys Val Ser Thr His Thr Ala Asn Phe Gly Gln
        265                 270                 275 cag gga gca tgt gaa ggt gtc tta ctg ctg act ctg gag gag aag aca        920
Gln Gly Ala Cys Glu Gly Val Leu Leu Leu Thr Leu Glu Glu Lys Thr
280                 285                 290 ttt cca gaa gat atg tgc tac cca gat caa ggt ggt gtc tgt cag ggc        968
Phe Pro Glu Asp Met Cys Tyr Pro Asp Gln Gly Gly Val Cys Gln Gly
295                 300                 305                 310 acg tgt gta gga ggt ggt ccc tac gca caa ggc gaa gat gcc agg atg       1016
Thr Cys Val Gly Gly Gly Pro Tyr Ala Gln Gly Glu Asp Ala Arg Met
                315                 320                 325 ctc tca ttg gtc agc aag acc gag ata gag gaa gac agc ttc aga cag       1064
Leu Ser Leu Val Ser Lys Thr Glu Ile Glu Glu Asp Ser Phe Arg Gln
            330                 335                 340 atg ccc aca gaa gat gaa tac atg gac agg ccc tcc cag ccc aca gac       1112
Met Pro Thr Glu Asp Glu Tyr Met Asp Arg Pro Ser Gln Pro Thr Asp
        345                 350                 355 cag tta ctg ttc ctc act gag cct gga agc aaa tcc aca cct cct ttc       1160
Gln Leu Leu Phe Leu Thr Glu Pro Gly Ser Lys Ser Thr Pro Pro Phe
    360                 365                 370 tct gaa ccc ctg gag gtg ggg gag aat gac agt tta agc cag tgc ttc       1208
Ser Glu Pro Leu Glu Val Gly Glu Asn Asp Ser Leu Ser Gln Cys Phe
375                 380                 385                 390 acg ggg aca cag agc aca gtg ggt tca gaa agc tgc aac tgc act gag       1256
Thr Gly Thr Gln Ser Thr Val Gly Ser Glu Ser Cys Asn Cys Thr Glu
                395                 400                 405 ccc ctg tgc agg act gat tgg act ccc atg tcc tct gaa aac tac ttg       1304
```

-continued

```
                Pro Leu Cys Arg Thr Asp Trp Thr Pro Met Ser Ser Glu Asn Tyr Leu
                            410                 415                 420 caa aaa gag gtg gac agt ggc cat tgc ccg cac tgg gca gcc agc ccc          1352
Gln Lys Glu Val Asp Ser Gly His Cys Pro His Trp Ala Ala Ser Pro
            425                 430                 435 agc ccc aac tgg gca gat gtc tgc aca ggc tgc cgg aac cct cct ggg          1400
Ser Pro Asn Trp Ala Asp Val Cys Thr Gly Cys Arg Asn Pro Pro Gly
    440                 445                 450 gag gac tgt gaa ccc ctc gtg ggt tcc cca aaa cgt gga ccc ttg ccc          1448
Glu Asp Cys Glu Pro Leu Val Gly Ser Pro Lys Arg Gly Pro Leu Pro
455                 460                 465                 470 cag tgc gcc tat ggc atg ggc ctt ccc cct gaa gaa gaa gcc agc agg          1496
Gln Cys Ala Tyr Gly Met Gly Leu Pro Pro Glu Glu Glu Ala Ser Arg
                475                 480                 485 acg gag gcc aga gac cag ccc gag gat ggg gct gat ggg agg ctc cca          1544
Thr Glu Ala Arg Asp Gln Pro Glu Asp Gly Ala Asp Gly Arg Leu Pro
            490                 495                 500 agc tca gcg agg gca ggt gcc ggg tct gga agc tcc cct ggt ggc cag          1592
Ser Ser Ala Arg Ala Gly Ala Gly Ser Gly Ser Ser Pro Gly Gly Gln
        505                 510                 515 tcc cct gca tct gga aat gtg act gga aac agt aac tcc acg ttc atc          1640
Ser Pro Ala Ser Gly Asn Val Thr Gly Asn Ser Asn Ser Thr Phe Ile
    520                 525                 530 tcc agc ggg cag gtg atg aac ttc aag ggc gac atc atc gtg gtc tac          1688
Ser Ser Gly Gln Val Met Asn Phe Lys Gly Asp Ile Ile Val Val Tyr
535                 540                 545                 550 gtc agc cag acc tcg cag gag ggc gcg gcg gcg gct gcg gag ccc atg          1736
Val Ser Gln Thr Ser Gln Glu Gly Ala Ala Ala Ala Ala Glu Pro Met
                555                 560                 565 ggc cgc ccg gtg cag gag gag acc ctg gcg cgc cga gac tcc ttc gcg          1784
Gly Arg Pro Val Gln Glu Glu Thr Leu Ala Arg Arg Asp Ser Phe Ala
            570                 575                 580 ggg aac ggc ccg cgc ttc ccg gac ccg tgc ggc ggc ccc gag ggg ctg          1832
Gly Asn Gly Pro Arg Phe Pro Asp Pro Cys Gly Gly Pro Glu Gly Leu
        585                 590                 595 cgg gag ccg gag aag gcc tcg agg ccg gtg cag gag caa ggc ggg gcc          1880
Arg Glu Pro Glu Lys Ala Ser Arg Pro Val Gln Glu Gln Gly Gly Ala
    600                 605                 610 aag gct tga gcgccccca tgctgggag cccgaagctc ggagccaggg                    1929
Lys Ala
615 ctcgcgaggg cagcaccgca gcctctgccc cagccccggc cacccaggga tcgatcggta        1989 cagtcgagga agaccacccg gcattctctg cccactttgc cttccaggaa atgggctttt        2049 caggaagtga attgatgagg actgtcccca tgcccacgga tgctcagcag cccgccgcac        2109 tggggcagat gtctcccctg ccactcctca aactcgcagc agtaatttgt ggcactatga        2169 cagctatttt tatgactatc ctgttctgtg gggggggggt ctatgttttc ccccatatt        2229 tgtattcctt ttcataactt ttcttgatat ctttcctccc tcttttttaa tgtaaaggtt       2289 ttctcaaaaa ttctcctaaa ggtgagggtc tctttctttt ctcttttcct ttttttttc         2349 ttttttttggc aacctggctc tggcccaggc tagagtgcag tggtgcgatt atagcccggt        2409 gcagcctcta actcctgggc tcaagcaatc caagtgatcc tcccacctca accttcggag        2469 tagctgggat cacagctgca ggccacgccc agcttcctcc ccccgactcc ccccccccag        2529 agacacggtc ccaccatgtt acccagcctg gtctcaaact cccagctaa agcagtcctc         2589 cagcctcggc ctcccaaagt actgggatta caggcgtgag cccccacgct ggcctgcttt        2649 acgtattttc ttttgtgccc ctgctcacag tgttttagag atggctttcc cagtgtgtgt        2709
```

-continued

```
tcattgtaaa cacttttggg aaagggctaa acatgtgagg cctggagata gttgctaagt   2769
tgctaggaac atgtggtggg actttcatat tctgaaaaat gttctatatt ctcattttc    2829 taaaagaaag aaaaaaggaa acccgattta tttctcctga atcttttta gtttgtgtcg    2889 ttccttaagc agaactaagc tcagtatgtg accttacccg ctaggtggtt aatttatcca   2949
tgctggcaga ggcactcagg tacttggtaa gcaaatttct aaaactccaa gttgctgcag   3009
cttggcattc ttcttattct agaggtctct ctggaaaaga tggagaaaat gaacaggaca   3069
tggggctcct ggaaagaaag ggcccgggaa gttcaaggaa gaataaagtt gaaattttaa   3129
aaaaaaa                                                             3136
```

<210> SEQ ID NO 2
<211> LENGTH: 616
<212> TYPE: PRT
<213> ORGANISM: Homo sapiens

<400> SEQUENCE: 2

```
Met Ala Pro Arg Ala Arg Arg Arg Pro Leu Phe Ala Leu Leu Leu
1               5                   10                  15

Leu Cys Ala Leu Leu Ala Arg Leu Gln Val Ala Leu Gln Ile Ala Pro
            20                  25                  30

Pro Cys Thr Ser Glu Lys His Tyr Glu His Leu Gly Arg Cys Cys Asn
        35                  40                  45

Lys Cys Glu Pro Gly Lys Tyr Met Ser Ser Lys Cys Thr Thr Thr Ser
    50                  55                  60

Asp Ser Val Cys Leu Pro Cys Gly Pro Asp Glu Tyr Leu Asp Ser Trp
65                  70                  75                  80

Asn Glu Glu Asp Lys Cys Leu Leu His Lys Val Cys Asp Thr Gly Lys
                85                  90                  95

Ala Leu Val Ala Val Ala Gly Asn Ser Thr Thr Pro Arg Arg Cys
            100                 105                 110

Ala Cys Thr Ala Gly Tyr His Trp Ser Gln Asp Cys Glu Cys Cys Arg
        115                 120                 125

Arg Asn Thr Glu Cys Ala Pro Gly Leu Gly Ala Gln His Pro Leu Gln
    130                 135                 140

Leu Asn Lys Asp Thr Val Cys Lys Pro Cys Leu Ala Gly Tyr Phe Ser
145                 150                 155                 160

Asp Ala Phe Ser Ser Thr Asp Lys Cys Arg Pro Trp Thr Asn Cys Thr
                165                 170                 175

Phe Leu Gly Lys Arg Val Glu His His Gly Thr Glu Lys Ser Asp Ala
            180                 185                 190

Val Cys Ser Ser Ser Leu Pro Ala Arg Lys Pro Pro Asn Glu Pro His
        195                 200                 205

Val Tyr Leu Pro Gly Leu Ile Ile Leu Leu Leu Phe Ala Ser Val Ala
    210                 215                 220

Leu Val Ala Ala Ile Ile Phe Gly Val Cys Tyr Arg Lys Lys Gly Lys
225                 230                 235                 240

Ala Leu Thr Ala Asn Leu Trp His Trp Ile Asn Glu Ala Cys Gly Arg
                245                 250                 255

Leu Ser Gly Asp Lys Glu Ser Ser Gly Asp Ser Cys Val Ser Thr His
            260                 265                 270

Thr Ala Asn Phe Gly Gln Gln Gly Ala Cys Glu Gly Val Leu Leu Leu
        275                 280                 285

Thr Leu Glu Glu Lys Thr Phe Pro Glu Asp Met Cys Tyr Pro Asp Gln
```

```
                290                 295                 300
Gly Gly Val Cys Gln Gly Thr Cys Val Gly Gly Pro Tyr Ala Gln
305                 310                 315                 320

Gly Glu Asp Ala Arg Met Leu Ser Leu Val Ser Lys Thr Glu Ile Glu
                325                 330                 335

Glu Asp Ser Phe Arg Gln Met Pro Thr Glu Asp Glu Tyr Met Asp Arg
                340                 345                 350

Pro Ser Gln Pro Thr Asp Gln Leu Leu Phe Leu Thr Glu Pro Gly Ser
                355                 360                 365

Lys Ser Thr Pro Pro Phe Ser Glu Pro Leu Glu Val Gly Glu Asn Asp
370                 375                 380

Ser Leu Ser Gln Cys Phe Thr Gly Thr Gln Ser Thr Val Gly Ser Glu
385                 390                 395                 400

Ser Cys Asn Cys Thr Glu Pro Leu Cys Arg Thr Asp Trp Thr Pro Met
                405                 410                 415

Ser Ser Glu Asn Tyr Leu Gln Lys Glu Val Asp Ser Gly His Cys Pro
                420                 425                 430

His Trp Ala Ala Ser Pro Ser Pro Asn Trp Ala Asp Val Cys Thr Gly
            435                 440                 445

Cys Arg Asn Pro Pro Gly Glu Asp Cys Glu Pro Leu Val Gly Ser Pro
450                 455                 460

Lys Arg Gly Pro Leu Pro Gln Cys Ala Tyr Gly Met Gly Leu Pro Pro
465                 470                 475                 480

Glu Glu Glu Ala Ser Arg Thr Glu Ala Arg Asp Gln Pro Glu Asp Gly
                485                 490                 495

Ala Asp Gly Arg Leu Pro Ser Ser Ala Arg Ala Gly Ala Gly Ser Gly
                500                 505                 510

Ser Ser Pro Gly Gly Gln Ser Pro Ala Ser Gly Asn Val Thr Gly Asn
            515                 520                 525

Ser Asn Ser Thr Phe Ile Ser Ser Gly Gln Val Met Asn Phe Lys Gly
            530                 535                 540

Asp Ile Ile Val Val Tyr Val Ser Gln Thr Ser Gln Glu Gly Ala Ala
545                 550                 555                 560

Ala Ala Ala Glu Pro Met Gly Arg Pro Val Gln Glu Glu Thr Leu Ala
                565                 570                 575

Arg Arg Asp Ser Phe Ala Gly Asn Gly Pro Arg Phe Pro Asp Pro Cys
                580                 585                 590

Gly Gly Pro Glu Gly Leu Arg Glu Pro Glu Lys Ala Ser Arg Pro Val
            595                 600                 605

Gln Glu Gln Gly Gly Ala Lys Ala
610                 615

<210> SEQ ID NO 3
<211> LENGTH: 232
<212> TYPE: PRT
<213> ORGANISM: Homo sapiens

<400> SEQUENCE: 3

Glu Pro Arg Ser Cys Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
```

-continued

```
                    50                      55                      60
Asp Gly Val Glu Val His Asn Ala Lys Thr Lys Pro Arg Glu Gln
 65                      70                      75                      80

Tyr Asn Ser Thr Tyr Arg Val Val Ser Val Leu Thr Val Leu His Gln
                         85                      90                      95

Asp Trp Leu Asn Gly Lys Asp Tyr Lys Cys Lys Val Ser Asn Lys Ala
                        100                     105                     110

Leu Pro Ala Pro Met Gln Lys Thr Ile Ser Lys Ala Lys Gly Gln Pro
                        115                     120                     125

Arg Glu Pro Gln Val Tyr Thr Leu Pro Pro Ser Arg Asp Glu Leu Thr
                130                     135                     140

Lys Asn Gln Val Ser Leu Thr Cys Leu Val Lys Gly Phe Tyr Pro Arg
145                     150                     155                     160

His Ile Ala Val Glu Trp Glu Ser Asn Gly Gln Pro Glu Asn Asn Tyr
                        165                     170                     175

Lys Thr Thr Pro Pro Val Leu Asp Ser Asp Gly Ser Phe Phe Leu Tyr
                        180                     185                     190

Ser Lys Leu Thr Val Asp Lys Ser Arg Trp Gln Gln Gly Asn Val Phe
                        195                     200                     205

Ser Cys Ser Val Met His Glu Ala Leu His Asn His Tyr Thr Gln Lys
                210                     215                     220

Ser Leu Ser Leu Ser Pro Gly Lys
225                     230
```

```
<210> SEQ ID NO 4
<211> LENGTH: 1878
<212> TYPE: DNA
<213> ORGANISM: Murine
<220> FEATURE:
<221> NAME/KEY: CDS
<222> LOCATION: (1)..(1875)

<400> SEQUENCE: 4
```

```
atg gcc ccg cgc gcc cgg cgg cgc cgc cag ctg ccc gcg ccg ctg ctg     48
Met Ala Pro Arg Ala Arg Arg Arg Arg Gln Leu Pro Ala Pro Leu Leu
 1               5                  10                  15 gcg ctc tgc gtg ctg ctc gtt cca ctg cag gtg act ctc cag gtc act     96
Ala Leu Cys Val Leu Leu Val Pro Leu Gln Val Thr Leu Gln Val Thr
             20                  25                  30 cct cca tgc acc cag gag agg cat tat gag cat ctc gga cgg tgt tgc    144
Pro Pro Cys Thr Gln Glu Arg His Tyr Glu His Leu Gly Arg Cys Cys
         35                  40                  45 agc aga tgc gaa cca gga aag tac ctg tcc tct aag tgc act cct acc    192
Ser Arg Cys Glu Pro Gly Lys Tyr Leu Ser Ser Lys Cys Thr Pro Thr
     50                  55                  60 tcc gac agt gtg tgt ctg ccc tgt ggc ccc gat gag tac ttg gac acc    240
Ser Asp Ser Val Cys Leu Pro Cys Gly Pro Asp Glu Tyr Leu Asp Thr
 65                  70                  75                  80 tgg aat gaa gaa gat aaa tgc ttg ctg cat aaa gtc tgt gat gca ggc    288
Trp Asn Glu Glu Asp Lys Cys Leu Leu His Lys Val Cys Asp Ala Gly
                 85                  90                  95 aag gcc ctg gtg gcg gtg gat cct ggc aac cac acg gcc ccg cgt cgc    336
Lys Ala Leu Val Ala Val Asp Pro Gly Asn His Thr Ala Pro Arg Arg
            100                 105                 110 tgt gct tgc acg gct ggc tac cac tgg aac tca gac tgc gag tgc tgc    384
Cys Ala Cys Thr Ala Gly Tyr His Trp Asn Ser Asp Cys Glu Cys Cys
        115                 120                 125 cgc agg aac acg gag tgt gca cct ggc ttc gga gct cag cat ccc ttg    432
Arg Arg Asn Thr Glu Cys Ala Pro Gly Phe Gly Ala Gln His Pro Leu
```

-continued

```
              130                 135                 140
cag ctc aac aag gat acg gtg tgc aca ccc tgc ctc ctg ggc ttc ttc       480
Gln Leu Asn Lys Asp Thr Val Cys Thr Pro Cys Leu Leu Gly Phe Phe
145                 150                 155                 160 tca gat gtc ttt tcg tcc aca gac aaa tgc aaa cct tgg acc aac tgc       528
Ser Asp Val Phe Ser Ser Thr Asp Lys Cys Lys Pro Trp Thr Asn Cys
                165                 170                 175 acc ctc ctt gga aag cta gaa gca cac cag ggg aca acg gaa tca gat       576
Thr Leu Leu Gly Lys Leu Glu Ala His Gln Gly Thr Thr Glu Ser Asp
            180                 185                 190 gtg gtc tgc agc tct tcc atg aca ctg agg aga cca ccc aag gag gcc       624
Val Val Cys Ser Ser Ser Met Thr Leu Arg Arg Pro Pro Lys Glu Ala
        195                 200                 205 cag gct tac ctg ccc agt ctc atc gtt ctg ctc ctc ttc atc tct gtg       672
Gln Ala Tyr Leu Pro Ser Leu Ile Val Leu Leu Leu Phe Ile Ser Val
    210                 215                 220 gta gta gtg gct gcc atc atc ttc ggc gtt tac tac agg aag gga ggg       720
Val Val Val Ala Ala Ile Ile Phe Gly Val Tyr Tyr Arg Lys Gly Gly
225                 230                 235                 240 aaa gcg ctg aca gct aat ttg tgg aat tgg gtc aat gat gct tgc agt       768
Lys Ala Leu Thr Ala Asn Leu Trp Asn Trp Val Asn Asp Ala Cys Ser
                245                 250                 255 agt cta agt gga aat aag gag tcc tca ggg gac cgt tgt gct ggt tcc       816
Ser Leu Ser Gly Asn Lys Glu Ser Ser Gly Asp Arg Cys Ala Gly Ser
            260                 265                 270 cac tcg gca acc tcc agt cag caa gaa gtg tgt gaa ggt atc tta cta       864
His Ser Ala Thr Ser Ser Gln Gln Glu Val Cys Glu Gly Ile Leu Leu
        275                 280                 285 atg act cgg gag gag aag atg gtt cca gaa gac ggt gct gga gtc tgt       912
Met Thr Arg Glu Glu Lys Met Val Pro Glu Asp Gly Ala Gly Val Cys
    290                 295                 300 ggg cct gtg tgt gcg gca ggt ggg ccc tgg gca gaa gtc aga gat tct       960
Gly Pro Val Cys Ala Ala Gly Gly Pro Trp Ala Glu Val Arg Asp Ser
305                 310                 315                 320 agg acg ttc aca ctg gtc agc gag gtt gag acg caa gga gac ctc tcg      1008
Arg Thr Phe Thr Leu Val Ser Glu Val Glu Thr Gln Gly Asp Leu Ser
                325                 330                 335 agg aag att ccc aca gag gat gag tac acg gac cgg ccc tcg cag cct      1056
Arg Lys Ile Pro Thr Glu Asp Glu Tyr Thr Asp Arg Pro Ser Gln Pro
            340                 345                 350 tcg act ggt tca ctg ctc cta atc cag cag gga agc aaa tct ata ccc      1104
Ser Thr Gly Ser Leu Leu Leu Ile Gln Gln Gly Ser Lys Ser Ile Pro
        355                 360                 365 cca ttc cag gag ccc ctg gaa gtg ggg gag aac gac agt tta agc cag      1152
Pro Phe Gln Glu Pro Leu Glu Val Gly Glu Asn Asp Ser Leu Ser Gln
    370                 375                 380 tgt ttc acc ggg act gaa agc acg gtg gat tct gag ggc tgt gac ttc      1200
Cys Phe Thr Gly Thr Glu Ser Thr Val Asp Ser Glu Gly Cys Asp Phe
385                 390                 395                 400 act gag cct ccg agc aga act gac tct atg ccc gtg tcc cct gaa aag      1248
Thr Glu Pro Pro Ser Arg Thr Asp Ser Met Pro Val Ser Pro Glu Lys
                405                 410                 415 cac ctg aca aaa gaa ata gaa ggt gac agt tgc ctc ccc tgg gtg gtc      1296
His Leu Thr Lys Glu Ile Glu Gly Asp Ser Cys Leu Pro Trp Val Val
            420                 425                 430 agc tcc aac tca aca gat ggc tac aca ggc agt ggg aac act cct ggg      1344
Ser Ser Asn Ser Thr Asp Gly Tyr Thr Gly Ser Gly Asn Thr Pro Gly
        435                 440                 445 gag gac cat gaa ccc ttt cca ggg tcc ctg aaa tgt gga cca ttg ccc      1392
Glu Asp His Glu Pro Phe Pro Gly Ser Leu Lys Cys Gly Pro Leu Pro
```

```
                 450                 455                 460
cag tgt gcc tac agc atg ggc ttt ccc agt gaa gca gca agc atg    1440
Gln Cys Ala Tyr Ser Met Gly Phe Pro Ser Glu Ala Ala Ser Met
465                 470                 475                 480 gca gag gcg gga gta cgg ccc cag gac agg gct gat gag agg gga gcc    1488
Ala Glu Ala Gly Val Arg Pro Gln Asp Arg Ala Asp Glu Arg Gly Ala
                    485                 490                 495 tca ggg tcc ggg agc tcc ccc agt gac cag cca cct gcc tct ggg aac    1536
Ser Gly Ser Gly Ser Ser Pro Ser Asp Gln Pro Pro Ala Ser Gly Asn
                500                 505                 510 gtg act gga aac agt aac tcc acg ttc atc tct agc ggg cag gtg atg    1584
Val Thr Gly Asn Ser Asn Ser Thr Phe Ile Ser Ser Gly Gln Val Met
                515                 520                 525 aac ttc aag ggt gac atc atc gtg gtg tat gtc agc cag acc tcg cag    1632
Asn Phe Lys Gly Asp Ile Ile Val Val Tyr Val Ser Gln Thr Ser Gln
530                 535                 540 gag ggc ccg ggt tcc gca gag ccc gag tcg gag ccc gtg ggc cgc cct    1680
Glu Gly Pro Gly Ser Ala Glu Pro Glu Ser Glu Pro Val Gly Arg Pro
545                 550                 555                 560 gtg cag gag gag acg ctg gca cac aga gac tcc ttt gcg ggc acc gcg    1728
Val Gln Glu Glu Thr Leu Ala His Arg Asp Ser Phe Ala Gly Thr Ala
                565                 570                 575 ccg cgc ttc ccc gac gtc tgt gcc acc ggg gct ggg ctg cag gag cag    1776
Pro Arg Phe Pro Asp Val Cys Ala Thr Gly Ala Gly Leu Gln Glu Gln
                580                 585                 590 ggg gca ccc cgg cag aag gac ggg aca tcg cgg ccg gtg cag gag cag    1824
Gly Ala Pro Arg Gln Lys Asp Gly Thr Ser Arg Pro Val Gln Glu Gln
                595                 600                 605 ggt ggg gcg cag act tca ctc cat acc cag ggg tcc gga caa tgt gca    1872
Gly Gly Ala Gln Thr Ser Leu His Thr Gln Gly Ser Gly Gln Cys Ala
610                 615                 620 gaa tga                                                              1878
Glu
625

<210> SEQ ID NO 5
<211> LENGTH: 625
<212> TYPE: PRT
<213> ORGANISM: Murine

<400> SEQUENCE: 5

Met Ala Pro Arg Ala Arg Arg Arg Gln Leu Pro Ala Pro Leu Leu
1               5                   10                  15

Ala Leu Cys Val Leu Leu Val Pro Leu Gln Val Thr Leu Gln Val Thr
                20                  25                  30

Pro Pro Cys Thr Gln Glu Arg His Tyr Glu His Leu Gly Arg Cys Cys
                35                  40                  45

Ser Arg Cys Glu Pro Gly Lys Tyr Leu Ser Ser Lys Cys Thr Pro Thr
50                  55                  60

Ser Asp Ser Val Cys Leu Pro Cys Gly Pro Asp Glu Tyr Leu Asp Thr
65                  70                  75                  80

Trp Asn Glu Glu Asp Lys Cys Leu Leu His Lys Val Cys Asp Ala Gly
                85                  90                  95

Lys Ala Leu Val Ala Val Asp Pro Gly Asn His Thr Ala Pro Arg Arg
                100                 105                 110

Cys Ala Cys Thr Ala Gly Tyr His Trp Asn Ser Asp Cys Glu Cys Cys
                115                 120                 125

Arg Arg Asn Thr Glu Cys Ala Pro Gly Phe Gly Ala Gln His Pro Leu
130                 135                 140
```

-continued

Gln Leu Asn Lys Asp Thr Val Cys Thr Pro Cys Leu Gly Phe Phe
145                 150                 155                 160

Ser Asp Val Phe Ser Ser Thr Asp Lys Cys Lys Pro Trp Thr Asn Cys
                165                 170                 175

Thr Leu Leu Gly Lys Leu Glu Ala His Gln Thr Thr Glu Ser Asp
            180                 185                 190

Val Val Cys Ser Ser Ser Met Thr Leu Arg Arg Pro Lys Glu Ala
            195                 200                 205

Gln Ala Tyr Leu Pro Ser Leu Ile Val Leu Leu Phe Ile Ser Val
        210                 215                 220

Val Val Val Ala Ala Ile Ile Phe Gly Val Tyr Tyr Arg Lys Gly Gly
225                 230                 235                 240

Lys Ala Leu Thr Ala Asn Leu Trp Asn Trp Val Asn Asp Ala Cys Ser
                245                 250                 255

Ser Leu Ser Gly Asn Lys Glu Ser Ser Gly Asp Arg Cys Ala Gly Ser
            260                 265                 270

His Ser Ala Thr Ser Ser Gln Gln Glu Val Cys Glu Gly Ile Leu Leu
        275                 280                 285

Met Thr Arg Glu Glu Lys Met Val Pro Glu Asp Gly Ala Gly Val Cys
290                 295                 300

Gly Pro Val Cys Ala Ala Gly Gly Pro Trp Ala Glu Val Arg Asp Ser
305                 310                 315                 320

Arg Thr Phe Thr Leu Val Ser Glu Val Glu Thr Gln Gly Asp Leu Ser
            325                 330                 335

Arg Lys Ile Pro Thr Glu Asp Glu Tyr Thr Asp Arg Pro Ser Gln Pro
            340                 345                 350

Ser Thr Gly Ser Leu Leu Leu Ile Gln Gln Gly Ser Lys Ser Ile Pro
        355                 360                 365

Pro Phe Gln Glu Pro Leu Glu Val Gly Glu Asn Asp Ser Leu Ser Gln
        370                 375                 380

Cys Phe Thr Gly Thr Glu Ser Thr Val Asp Ser Glu Gly Cys Asp Phe
385                 390                 395                 400

Thr Glu Pro Pro Ser Arg Thr Asp Ser Met Pro Val Ser Pro Glu Lys
                405                 410                 415

His Leu Thr Lys Glu Ile Glu Gly Asp Ser Cys Leu Pro Trp Val Val
            420                 425                 430

Ser Ser Asn Ser Thr Asp Gly Tyr Thr Gly Ser Gly Asn Thr Pro Gly
        435                 440                 445

Glu Asp His Glu Pro Phe Pro Gly Ser Leu Lys Cys Gly Pro Leu Pro
450                 455                 460

Gln Cys Ala Tyr Ser Met Gly Phe Pro Ser Glu Ala Ala Ala Ser Met
465                 470                 475                 480

Ala Glu Ala Gly Val Arg Pro Gln Asp Arg Ala Asp Glu Arg Gly Ala
                485                 490                 495

Ser Gly Ser Gly Ser Ser Pro Ser Asp Gln Pro Pro Ala Ser Gly Asn
            500                 505                 510

Val Thr Gly Asn Ser Asn Ser Thr Phe Ile Ser Ser Gly Gln Val Met
        515                 520                 525

Asn Phe Lys Gly Asp Ile Ile Val Val Tyr Val Ser Gln Thr Ser Gln
        530                 535                 540

Glu Gly Pro Gly Ser Ala Glu Pro Glu Ser Glu Pro Val Gly Arg Pro
545                 550                 555                 560

Val Gln Glu Glu Thr Leu Ala His Arg Asp Ser Phe Ala Gly Thr Ala

```
                       565                 570                 575
Pro Arg Phe Pro Asp Val Cys Ala Thr Gly Ala Gly Leu Gln Glu Gln
                580                 585                 590

Gly Ala Pro Arg Gln Lys Asp Gly Thr Ser Arg Pro Val Gln Glu Gln
            595                 600                 605

Gly Gly Ala Gln Thr Ser Leu His Thr Gln Gly Ser Gly Gln Cys Ala
        610                 615                 620

Glu
625

<210> SEQ ID NO 6
<211> LENGTH: 33
<212> TYPE: PRT
<213> ORGANISM: Artificial sequence
<220> FEATURE:
<223> OTHER INFORMATION: Murine

<400> SEQUENCE: 6

Arg Met Lys Gln Ile Glu Asp Lys Ile Glu Ile Leu Ser Lys Ile
1               5                   10                  15

Tyr His Ile Glu Asn Glu Ile Ala Arg Ile Lys Lys Leu Ile Gly Glu
            20                  25                  30

Arg

<210> SEQ ID NO 7
<211> LENGTH: 954
<212> TYPE: DNA
<213> ORGANISM: Homo sapiens
<220> FEATURE:
<221> NAME/KEY: CDS
<222> LOCATION: (1)..(951)

<400> SEQUENCE: 7 atg cgc cgc gcc agc aga gac tac acc aag tac ctg cgt ggc tcg gag       48
Met Arg Arg Ala Ser Arg Asp Tyr Thr Lys Tyr Leu Arg Gly Ser Glu
1               5                   10                  15 gag atg ggc ggc ggc ccc gga gcc ccg cac gag ggc ccc ctg cac gcc       96
Glu Met Gly Gly Gly Pro Gly Ala Pro His Glu Gly Pro Leu His Ala
            20                  25                  30 ccg ccg ccg cct gcg ccg cac cag ccc ccc gcc gcc tcc cgc tcc atg      144
Pro Pro Pro Ala Pro His Gln Pro Pro Ala Ala Ser Arg Ser Met
        35                  40                  45 ttc gtg gcc ctc ctg ggg ctg ggg ctg gcc cag gtt gtc tgc agc gtc      192
Phe Val Ala Leu Leu Gly Leu Gly Leu Gly Gln Val Val Cys Ser Val
    50                  55                  60 gcc ctg ttc ttc tat ttc aga gcg cag atg gat cct aat aga ata tca      240
Ala Leu Phe Phe Tyr Phe Arg Ala Gln Met Asp Pro Asn Arg Ile Ser
65                  70                  75                  80 gaa gat ggc act cac tgc att tat aga att ttg aga ctc cat gaa aat      288
Glu Asp Gly Thr His Cys Ile Tyr Arg Ile Leu Arg Leu His Glu Asn
                85                  90                  95 gca gat ttt caa gac aca act ctg gag agt caa gat aca aaa tta ata      336
Ala Asp Phe Gln Asp Thr Thr Leu Glu Ser Gln Asp Thr Lys Leu Ile
            100                 105                 110 cct gat tca tgt agg aga att aaa cag gcc ttt caa gga gct gtg caa      384
Pro Asp Ser Cys Arg Arg Ile Lys Gln Ala Phe Gln Gly Ala Val Gln
        115                 120                 125 aag gaa tta caa cat atc gtt gga tca cag cac atc aga gca gag aaa      432
Lys Glu Leu Gln His Ile Val Gly Ser Gln His Ile Arg Ala Glu Lys
    130                 135                 140 gcg atg gtg gat ggc tca tgg tta gat ctg gcc aag agg agc aag ctt      480
```

```
Ala Met Val Asp Gly Ser Trp Leu Asp Leu Ala Lys Arg Ser Lys Leu
145                 150                 155                 160 gaa gct cag cct ttt gct cat ctc act att aat gcc acc gac atc cca      528
Glu Ala Gln Pro Phe Ala His Leu Thr Ile Asn Ala Thr Asp Ile Pro
                165                 170                 175 tct ggt tcc cat aaa gtg agt ctg tcc tct tgg tac cat gat cgg ggt      576
Ser Gly Ser His Lys Val Ser Leu Ser Ser Trp Tyr His Asp Arg Gly
                180                 185                 190 tgg gcc aag atc tcc aac atg act ttt agc aat gga aaa cta ata gtt      624
Trp Ala Lys Ile Ser Asn Met Thr Phe Ser Asn Gly Lys Leu Ile Val
                195                 200                 205 aat cag gat ggc ttt tat tac ctg tat gcc aac att tgc ttt cga cat      672
Asn Gln Asp Gly Phe Tyr Tyr Leu Tyr Ala Asn Ile Cys Phe Arg His
210                 215                 220 cat gaa act tca gga gac cta gct aca gag tat ctt caa cta atg gtg      720
His Glu Thr Ser Gly Asp Leu Ala Thr Glu Tyr Leu Gln Leu Met Val
225                 230                 235                 240 tac gtc act aaa acc agc atc aaa atc cca agt tct cat acc ctg atg      768
Tyr Val Thr Lys Thr Ser Ile Lys Ile Pro Ser Ser His Thr Leu Met
                245                 250                 255 aaa gga gga agc acc aag tat tgg tca ggg aat tct gaa ttc cat ttt      816
Lys Gly Gly Ser Thr Lys Tyr Trp Ser Gly Asn Ser Glu Phe His Phe
                260                 265                 270 tat tcc ata aac gtt ggt gga ttt ttt aag tta cgg tct gga gag gaa      864
Tyr Ser Ile Asn Val Gly Gly Phe Phe Lys Leu Arg Ser Gly Glu Glu
                275                 280                 285 atc agc atc gag gtc tcc aac ccc tcc tta ctg gat ccg gat cag gat      912
Ile Ser Ile Glu Val Ser Asn Pro Ser Leu Leu Asp Pro Asp Gln Asp
                290                 295                 300 gca aca tac ttt ggg gct ttt aaa gtt cga gat ata gat tga              954
Ala Thr Tyr Phe Gly Ala Phe Lys Val Arg Asp Ile Asp
305                 310                 315

<210> SEQ ID NO 8
<211> LENGTH: 317
<212> TYPE: PRT
<213> ORGANISM: Homo sapiens

<400> SEQUENCE: 8

Met Arg Arg Ala Ser Arg Asp Tyr Thr Lys Tyr Leu Arg Gly Ser Glu
1               5                   10                  15

Glu Met Gly Gly Gly Pro Gly Ala Pro His Glu Gly Pro Leu His Ala
                20                  25                  30

Pro Pro Pro Pro Ala Pro His Gln Pro Pro Ala Ala Ser Arg Ser Met
            35                  40                  45

Phe Val Ala Leu Leu Gly Leu Gly Leu Gly Gln Val Val Cys Ser Val
    50                  55                  60

Ala Leu Phe Phe Tyr Phe Arg Ala Gln Met Asp Pro Asn Arg Ile Ser
65                  70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125

Lys Glu Leu Gln His Ile Val Gly Ser Gln His Ile Arg Ala Glu Lys
    130                 135                 140

Ala Met Val Asp Gly Ser Trp Leu Asp Leu Ala Lys Arg Ser Lys Leu
145                 150                 155                 160
```

```
                                            -continued

Glu Ala Gln Pro Phe Ala His Leu Thr Ile Asn Ala Thr Asp Ile Pro
            165                 170                 175

Ser Gly Ser His Lys Val Ser Leu Ser Ser Trp Tyr His Asp Arg Gly
            180                 185                 190

Trp Ala Lys Ile Ser Asn Met Thr Phe Ser Asn Gly Lys Leu Ile Val
        195                 200                 205

Asn Gln Asp Gly Phe Tyr Tyr Leu Tyr Ala Asn Ile Cys Phe Arg His
        210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
                260                 265                 270

Tyr Ser Ile Asn Val Gly Gly Phe Phe Lys Leu Arg Ser Gly Glu Glu
            275                 280                 285

Ile Ser Ile Glu Val Ser Asn Pro Ser Leu Leu Asp Pro Asp Gln Asp
        290                 295                 300

Ala Thr Tyr Phe Gly Ala Phe Lys Val Arg Asp Ile Asp
305                 310                 315
```

METHOD OF INHIBITING OSTEOCLAST ACTIVITY

CROSS-REFERENCE TO RELATED PATENT APPLICATIONS

This application is a continuation of U.S. patent application Ser. No. 12/137,397, filed Jun. 11, 2008, now U.S. Pat. No. 7,790,684, which is incorporated herein in its entirety, which is a continuation of U.S. patent application Ser. No. 09/705,985 filed Nov. 3, 2000, now abandoned, which is a continuation of International patent application No. PCT/US99/10588 filed May 13, 1999, which claims the benefit of U.S. provisional patent applications 60/110,836 filed Dec. 3, 1998 and 60/085,487 filed May 14, 1998, and is a continuation-in-part of U.S. patent application Ser. No. 11/881,911 filed Jul. 30, 2007, pending, which is a divisional of U.S. patent application Ser. No. 10/405,878 filed Apr. 1, 2003, now U.S. Pat. No. 7,262,274, which is a continuation of U.S. patent application Ser. No. 09/871,291 filed May 30, 2001, now U.S. Pat. No. 6,562,948, which is a divisional of U.S. patent application Ser. No. 09/577,800 filed May 24, 2000, now U.S. Pat. No. 6,479,635, which is a continuation of U.S. patent application Ser. No. 09/466,496 filed Dec. 17, 1999, now U.S. Pat. No. 6,528,482, which is a continuation of U.S. patent application Ser. No. 08/996,139 filed Dec. 22, 1997, now U.S. Pat. No. 6,017,729, which claims the benefit of U.S. provisional application No. 60/064,671 filed Oct. 14, 1997, U.S. provisional application No. 60/077,181 filed Mar. 7, 1997, and U.S. provisional application No. 60/059,978, filed Dec. 23, 1996.

REFERENCE TO THE SEQUENCE LISTING

The present application is being filed along with a Sequence Listing in electronic format. The Sequence Listing is provided as a file entitled 2874-US-CNT5_SEQ_ST25.txt, created Aug. 3, 2010, which is 41 KB in size. The information in the electronic format of the Sequence Listing is incorporated herein by reference in its entirety.

TECHNICAL FIELD OF THE INVENTION

The present invention relates generally to the field of cytokine receptors, and more specifically to cytokine receptor/ligand pairs having osteoclast regulatory activity.

BACKGROUND OF THE INVENTION

RANK (Receptor Activator of NF-κB) and its ligand (RANKL) are a recently-described receptor/ligand pair that play an important role in an immune response. The cloning of RANK and RANKL is described in U.S. Ser. No. 08/996,139 and U.S. Ser. No. 08/995,659, respectively. It has recently been found that RANKL binds to a protein referred to as osteoprotegerin (OPG), a member of the Tumor Necrosis Factor Receptor (TNFR) family. Yasuda et al. (*Proc. Natl. Acad. Sci.* 95:3597; 1998) expression cloned a ligand for OPG, which they referred to as osteoclastogenesis inhibitory factor. Their work was repeated by Lacey et al. (*Cell* 93:165; 1998). In both cases, the ligand they cloned turned out to be identical to RANKL.

In osteoclastogenesis, the interaction of an osteoblast or stromal cell with an osteoclast precursor leads to the differentiation of the precursor into an osteoclast. OPG was known to inhibit this differentiation. A model has been proposed in which RANKL on the osteoblast or stromal cell surface interacts with a specific receptor on an osteoclast progenitor surface, signaling a differentiation event. OPG effectively blocks the interaction of RANKL with a receptor on osteoclast progenitors in vitro, and has been shown to ameliorate the effects of ovariectomy on bone-loss in mice. However, OPG is also known to bind other ligands in the TNF family, which may have a deleterious effect on the activities of such ligands in vivo. Moreover, the presence of other ligands that bind OPG in vivo may require high dosages of OPG to be administered in order to have sufficient soluble OPG available to inhibit osteoclastogenesis.

Accordingly, there is a need in the art to identify soluble factors that specifically bind RANKL and inhibit the ability of RANKL to induce osteoclastogenesis without reacting with other ligands.

SUMMARY OF THE INVENTION

The present invention provides processes associated with the use of a novel receptor, referred to as RANK (for receptor activator of NF-κB), that is a member of the TNF receptor superfamily. RANK is a Type I transmembrane protein having 616 amino acid residues, comprising an extracellular domain, transmembrane region and cytoplasmic domain. RANK interacts with various TNF Receptor Associated Factors (TRAFs); triggering of RANK results in the upregulation of the transcription factor NF-κB, a ubiquitous transcription factor that is most extensively utilized in cells of the immune system.

Soluble forms of the receptor can be prepared and used to interfere with signal transduction through membrane-bound RANK. Inhibition of RANKL-mediated signal transduction will be useful in ameliorating the effects of osteoclastogenesis and osteoclast activity in disease conditions in which there is excess bone break down. Examples of such conditions include osteoporosis, Paget's disease, cancers that may metastasize to bone and induce bone breakdown (i.e., multiple myeloma, breast cancer, some melanomas; see also Mundy, C. *Cancer Suppl.* 80:1546; 1997), and cancers that do not necessarily metastasize to bone, but result in hypercalcemia and bone loss (e.g. squamous cell carcinomas).

Soluble forms of RANK comprise the extracellular domain of RANK or a fragment thereof that binds RANKL. Fusion proteins of RANK may be made to allow preparation of soluble RANK. Examples of such fusion proteins include a RANK/Fc fusion protein, a fusion protein of a zipper moiety (i.e., a leucine zipper), and various tags that are known in the art. Other antagonists of the interaction of RANK and RANKL (i.e., antibodies to RANKL, small molecules) will also be useful in the inventive methods. These and other aspects of the present invention will become evident upon reference to the following detailed description of the invention.

DETAILED DESCRIPTION OF THE INVENTION

A novel partial cDNA insert with a predicted open reading frame having some similarity to CD40 was identified and was used to hybridize to colony blots generated from a dendritic cell (DC) cDNA library containing full-length cDNAs. SEQ ID NO:1 shows the nucleotide and amino acid sequence of a predicted full-length protein.

RANK is a member of the TNF receptor superfamily; it most closely resembles CD40 in the extracellular region. RANK is expressed on epithelial cells, some B cell lines, and on activated T cells. However, its expression on activated T cells is late, about four days after activation. This time course of expression coincides with the expression of Fas, a known agent of apoptosis. RANK may act as an anti-apoptotic signal, rescuing cells that express RANK from apoptosis as CD40 is known to do. Alternatively, RANK may confirm an apoptotic signal under the appropriate circumstances, again similar to CD40. RANK and its ligand are likely to play an integral role in regulation of the immune and inflammatory response. The isolation of a DNA encoding RANK is described in U.S. Ser. No. 08/996,139, filed Dec. 22, 1997, the disclosure of which is incorporated by reference herein. U.S. Ser. No. 08/996,139 describes several forms of RANK that are useful in the present invention.

Soluble RANK comprises the signal peptide and the extracellular domain (residues 1 to 213 of SEQ ID NO:2) or a fragment thereof. Alternatively, a different signal peptide can be substituted for the native leader, beginning with residue 1 and continuing through a residue selected from the group consisting of amino acids 24 through 33 (inclusive) of SEQ ID NO:2. Other members of the TNF receptor superfamily have a region of amino acids between the transmembrane domain and the ligand binding domain that is referred to as a 'spacer' region, which is not necessary for ligand binding. In RANK, the amino acids between 196 and 213 are predicted to form such a spacer region. Accordingly, a soluble form of RANK that terminates with an amino acid in this region is expected to retain the ability to bind a ligand for RANK in a specific manner. Preferred C-terminal amino acids for soluble RANK peptides are selected from the group consisting of amino acids 213 and 196 of SEQ ID NO:2, although other amino acids in the spacer region may be utilized as a C-terminus. In muRANK, the amino acids between 197 and 214 are predicted to form such a spacer region. Accordingly, a soluble form of RANK that terminates with an amino acid in this region is expected to retain the ability to bind a ligand for RANK in a specific manner. Preferred C-terminal amino acids for soluble RANK peptides are selected from the group consisting of amino acids 214, and 197 of SEQ ID NO:5, although other amino acids in the spacer region may be utilized as a C-terminus. Moreover, fragments of the extracellular domain will also provide soluble forms of RANK.

Fragments can be prepared using known techniques to isolate a desired portion of the extracellular region, and can be prepared, for example, by comparing the extracellular region with those of other members of the TNFR family (of which RANK is a member) and selecting forms similar to those prepared for other family members. Alternatively, unique restriction sites or PCR techniques that are known in the art can be used to prepare numerous truncated forms which can be expressed and analyzed for activity.

Other derivatives of the RANK proteins within the scope of this invention include covalent or aggregative conjugates of the proteins or their fragments with other proteins or polypeptides, such as by synthesis in recombinant culture as N-terminal or C-terminal fusions. For example, the conjugated peptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast a-factor leader).

Protein fusions can comprise peptides added to facilitate purification or identification of RANK proteins and homologs (e.g., poly-His). The amino acid sequence of the inventive proteins can also be linked to an identification peptide such as that described by Hopp et al., Bio/Technology 6:1204 (1988; FLAG™). Such a highly antigenic peptide provides an epitope reversibly bound by a specific monoclonal antibody, enabling rapid assay and facile purification of expressed recombinant protein. The sequence of Hopp et al. is also specifically cleaved by bovine mucosal enterokinase, allowing removal of the peptide from the purified protein.

Fusion proteins further comprise the amino acid sequence of a RANK linked to an immunoglobulin Fc region. An exemplary Fc region is a human $IgG_1$ having an amino acid sequence set forth in SEQ ID NO:3. Fragments of an Fc region may also be used, as can Fc muteins. For example, certain residues within the hinge region of an Fc region are critical for high affinity binding to FcγRI. Canfield and Morrison (J. Exp. Med. 173:1483; 1991) reported that $Leu_{(234)}$ and $Leu_{(235)}$ were critical to high affinity binding of $IgG_3$ to FcγRI present on U937 cells. Similar results were obtained by Lund et al. (J. Immunol. 147:2657, 1991; Molecular Immunol. 29:53, 1991). Such mutations, alone or in combination, can be made in an $IgG_1$ Fc region to decrease the affinity of $IgG_1$ for FcR. Depending on the portion of the Fc region used, a fusion protein may be expressed as a dimer, through formation of interchain disulfide bonds. If the fusion proteins are made with both heavy and light chains of an antibody, it is possible to form a protein oligomer with as many as four RANK regions.

In another embodiment, RANK proteins further comprise an oligomerizing peptide such as a zipper domain. Leucine zippers were originally identified in several DNA-binding proteins (Landschulz et al., Science 240:1759, 1988). Zipper domain is a term used to refer to a conserved peptide domain present in these (and other) proteins, which is responsible for multimerization of the proteins. The zipper domain comprises a repetitive heptad repeat, with four or five leucine, isoleucine or valine residues interspersed with other amino acids. Examples of zipper domains are those found in the yeast transcription factor GCN4 and a heat-stable DNA-binding protein found in rat liver (C/EBP; Landschulz et al., Science 243:1681, 1989). Two nuclear transforming proteins, fos and jun, also exhibit zipper domains, as does the gene product of the murine proto-oncogene, c-myc (Landschulz et al., Science 240:1759, 1988). The products of the nuclear oncogenes fos and jun comprise zipper domains that preferentially form a heterodimer (O'Shea et al., Science 245:646, 1989; Turner and Tjian, Science 243:1689, 1989). A preferred zipper moiety is that of SEQ ID NO:6 or a fragment thereof. This and other zippers are disclosed in U.S. Pat. No. 5,716, 805.

Other embodiments of useful proteins include RANK polypeptides encoded by DNAs capable of hybridizing to the DNA of SEQ ID NO:1 under moderately stringent conditions (prewashing solution of 5×SSC, 0.5% SDS, 1.0 mM EDTA (pH 8.0) and hybridization conditions of 50° C., 5×SSC, overnight) to the DNA sequences encoding RANK, or more preferably under stringent conditions (for example, hybridization in 6×SSC at 63° C. overnight; washing in 3×SSC at 55° C.), and other sequences which are degenerate to those which encode the RANK. In one embodiment, RANK polypeptides are at least about 70% identical in amino acid sequence to the amino acid sequence of native RANK protein as set forth in SEQ ID NO:2 for human RANK and NO:5 for murine RANK. In a preferred embodiment, RANK polypeptides are at least about 80% identical in amino acid sequence to the native form of RANK; most preferred polypeptides are those that are at least about 90% identical to native RANK.

Percent identity may be determined using a computer program, for example, the GAP computer program described by Devereux et al. (Nucl. Acids Res. 12:387, 1984) and available from the University of Wisconsin Genetics Computer Group (UWGCG). For fragments derived from the RANK protein, the identity is calculated based on that portion of the RANK protein that is present in the fragment The biological activity of RANK analogs or muteins can be determined by testing the ability of the analogs or muteins to bind RANKL (SEQ ID NOS:7 and 8), for example as described in the Examples herein. Suitable assays include, for example, an enzyme immunoassay or a dot blot, and assays that employ cells expressing RANKL. Suitable assays also include, for example, inhibition assays, wherein soluble RANK is used to inhibit the interaction of RANKL with membrane-bound or solid-phase associated RANK (i.e., signal transduction assays). Such methods are well known in the art.

RANKL and RANK are important factors in osteoclastogenesis. RANK is expressed on osteoclasts and interacts with RANK ligand (RANKL) to mediate the formation of osteoclast-like (OCL) multinucleated cells. This was shown by treating mouse bone marrow preparations with M-CSF (CSF-1) and soluble RANKL for 7 days in culture. No additional osteoclastogenic hormones or factors were necessary for the generation of the multinucleated cells. Neither M-CSF nor RANKL alone led to the formation of OCL. The multinucleated cells expressed tartrate resistant acid phosphatase and were positive for $[^{125}I]$-calcitonin binding. The tyrosine kinase c-src was highly expressed in multinucleated OCL and a subset of mononuclear cells as demonstrated by immunofluorescence microscopy. (See Example 2).

Purification of Recombinant RANK

Purified RANK, and homologs or analogs thereof are prepared by culturing suitable host/vector systems to express the recombinant translation products of the DNAs of the present invention, which are then purified from culture media or cell extracts. For example, supernatants from systems which secrete recombinant protein into culture media can be first concentrated using a commercially available protein concentration filter, for example, an Amicon or Millipore Pellicon ultrafiltration unit.

Following the concentration step, the concentrate can be applied to a suitable purification matrix. For example, a suitable affinity matrix can comprise a counter structure protein or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Gel filtration chromatography also provides a means of purifying the inventive proteins.

Affinity chromatography is a particularly preferred method of purifying RANK and homologs thereof. For example, a RANK expressed as a fusion protein comprising an immunoglobulin Fc region can be purified using Protein A or Protein G affinity chromatography. Moreover, a RANK protein comprising an oligomerizing zipper domain may be purified on a resin comprising an antibody specific to the oligomerizing zipper domain. Monoclonal antibodies against the RANK protein may also be useful in affinity chromatography purification, by utilizing methods that are well-known in the art. A ligand may also be used to prepare an affinity matrix for affinity purification of RANK.

Finally, one or more reversed-phase high performance liquid chromatography (RP-HPLC) steps employing hydrophobic RP-HPLC media, e.g., silica gel having pendant methyl or other aliphatic groups, can be employed to further purify a RANK composition. Suitable methods include those analogous to the method disclosed by Urdal et al. (*J. Chromatog.* 296:171, 1984). Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant protein can be disrupted by any convenient method, including freeze-thaw cycling, sonication, mechanical disruption, or use of cell lysing agents.

Fermentation of yeast which express the inventive protein as a secreted protein greatly simplifies purification.

Protein synthesized in recombinant culture is characterized by the presence of cell components, including proteins, in amounts and of a character which depend upon the purification steps taken to recover the inventive protein from the culture. These components ordinarily will be of yeast, prokaryotic or non-human higher eukaryotic origin and preferably are present in innocuous contaminant quantities, on the order of less than about 1 percent by weight. Further, recombinant cell culture enables the production of the inventive proteins free of other proteins which may be normally associated with the proteins as they are found in nature in the species of origin.

Uses and Administration of RANK Compositions

The present invention provides methods of using therapeutic compositions comprising a protein and a suitable diluent and carrier. These methods involve the use of therapeutic compositions of RANK or soluble fragments of RANK for regulating an immune or inflammatory response. Further included within the present invention are methods for regulating osteoclast activity by administering therapeutic compositions of RANK or soluble RANK fragments to an individual in amounts sufficient to decrease excess bone resorption. Typically, the individual is inflicted with excess bone resorption and suffers from the effects of hypercalcemia, has symptoms of hypercalcemia, or is suffering a disease that involves excessive bone resorption. In addition to regulating osteoclast activity, the methods described herein are applicable to inhibiting osteoclast activity, regulating osteoclast generation and inhibiting osteoclast generation in individuals inflicted with excess bone resorption. In connection with the methods described herein, the present invention contemplates the use of RANK in conjunction with soluble cytokine receptors or cytokines, or other osteoclast/osteoblast regulatory molecules.

Soluble forms of RANK and other RANK antagonists such as antagonistic monoclonal antibodies can be administered for the purpose of inhibiting RANK-induced induction of NF-κB activity. NF-κB is a transcription factor that is utilized extensively by cells of the immune system, and plays a role in the inflammatory response. Thus, inhibitors of RANK signalling will be useful in treating conditions in which signalling through RANK has given rise to negative consequences, for example, toxic or septic shock, or graft-versus-host reactions. They may also be useful in interfering with the role of NF-κB in cellular transformation. Tumor cells are more responsive to radiation when their NF-κB is blocked; thus, soluble RANK (or other antagonists of RANK signalling) will be useful as an adjunct therapy for disease characterized by neoplastic cells that express RANK.

In connection with the methods described herein, RANK ligand (RANKL) on osteoblasts or stromal cells is known to interact with RANK on osteoclast progenitor surfaces signaling an event that leads to the differentiation of osteoclast precursors into osteoclasts. (See Example 2 below.) Thus, RANK, and in particular soluble forms of RANK, is useful for the inhibition of the RANKL-mediated signal transduction that leads to the differentiation of osteoclast precursors into osteoclasts. Soluble forms of RANK are also useful for the regulation and inhibition of osteoclast activity, e.g. bone resorption. By interfering with osteoclast differentiation, soluble forms of RANK are useful in the amelioration of the effects of osteoclastogenesis in disease conditions in which there is excess bone break down. Such disease conditions include Paget's disease, osteoporosis, and cancer. Many cancers metastasize to bone and induce bone breakdown by locally disrupting normal bone remodeling. Such cancers can be associated with enhanced numbers of osteoclasts and enhanced amount of osteoclastic bone resorption resulting in hypercalcemia. These cancers include, but are not limited to, breast cancer, multiple myeloma, melanomas, lung cancer, prostrate, hematologic, head and neck, and renal. (See Guise et al. *Endocrine Reviews,* 19(1):18-54, 1998.) Soluble forms of RANK can be administered to such cancer patients to disrupt the osteoclast differentiation pathway and result in fewer numbers of osteoclast, less bone resorption, and relief from the negative effects of hypercalcemia.

Other cancers do not metastasize to bone, but are known to act systemically on bone to disrupt bone remodeling and result in hypercalcemia. (See Guise et al. Endocrine Reviews, 19(1):18-54, 1998.) In accordance with this invention, RANKL has been found on the surface of certain squamous cells that do not metastasize to bone but are associated with hypercalcemia. (See Example 3 below) Squamous cells that are associated with hypercalcemia also express M-CSF (CSF-1), a cytokine that, together with RANKL, stimulates the proliferation and differentiation of osteoclast precursors to osteoclasts. In accordance with the present invention, it has been discovered that M-CSF directly upregulates RANK on surfaces of osteoclast precursors. When squamous cells release excessive amounts of CSF-1, increased expression of RANK occurs on the surfaces of osteoclast precursors. Thus, there is a higher probability that RANK will interact with RANKL on osteoblasts or stromal cells to produce increased numbers of osteoclasts, resulting in an enhanced amount of bone break down and hypercalcemia.

In addition to the ameliorating the effects of cancers that metastasize to bone, the present invention provides methods for ameliorating the systemic effects, e.g. hypercalcemia, of cancers that are associated with excess osteoclast activity (e.g. squamous cell carcinomas). Such methods include administering soluble forms of RANK in amounts sufficient to interfere with the RANK/RANKL signal transduction that leads to the differentiation of osteoclast precursors into osteoclasts. Fewer osteoclasts lead to reduced bone resorption and relief from the negative effects of hypercalcemia.

For therapeutic use, purified protein is administered to an individual, preferably a human, for treatment in a manner appropriate to the indication. Thus, for example, RANK protein compositions administered to regulate osteoclast function can be given by bolus injection, continuous infusion, sustained release from implants, or other suitable technique. Typically, a therapeutic agent will be administered in the form of a composition comprising purified RANK, in conjunction with physiologically acceptable carriers, excipients or diluents. Such carriers will be nontoxic to recipients at the dosages and concentrations employed.

Ordinarily, the preparation of such protein compositions entails combining the inventive protein with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with con-specific serum albumin are exemplary appropriate diluents. Preferably, product is formulated as a lyophilizate using appropriate excipient solutions (e.g., sucrose) as diluents. Appropriate dosages can be determined in trials. The amount and frequency of administration will depend, of course, on such factors as the nature and severity of the indication being treated, the desired response, the condition of the patient, and so forth.

Soluble forms of RANK and other RANK antagonists such as antagonistic monoclonal antibodies can be administered for the purpose of inhibiting RANK-induced osteoclastogenesis. It is desirable to inhibit osteoclastogenesis in various disease states in which excess bone loss occurs. Examples include osteoporosis, Pagett's disease, and various cancers. Various animal models of these diseases are known in the art; accordingly, it is a matter of routine experimentation to determine optimal dosages and routes of administration of soluble RANK, first in an animal model and then in human clinical trials.

The following examples are offered by way of illustration, and not by way of limitation. Those skilled in the art will recognize that variations of the invention embodied in the examples can be made, especially in light of the teachings of the various references cited herein, the disclosures of which are incorporated by reference.

EXAMPLE 1

This example describes a plate binding assay useful in comparing the ability of various ligands to bind receptors. The assay is performed essentially as described in Smith et al., Virology 236:316 (1997). Briefly, 96-well microtiter plates are coated with an antibody to human Fc (i.e., polyclonal goat anti human Fc). Receptor/Fc fusion proteins are then added, and after incubation, the plates are washed. Serial dilutions of the ligands are then added. The ligands may be directly labeled (i.e., with $^{125}$I), or a detecting reagent that is radioactively labeled may be used. After incubation, the plates are washed, specifically bound ligands are released, and the amount of ligand bound quantified.

Using this method, RANK/Fc and OPG/Fc were bound to 96-well plates. In an indirect method, a RANKL/zipper fusion is detected using a labeled antibody to the zipper moiety. It was found that human OPG/Fc binds mRANKL at 0.05 nM, and human RANK/Fc binds mRANKL at 0.1 nM. These values indicate similar binding affinities of OPG and RANK for RANKL, confirming the utility of RANK as an inhibitor of osteoclast activity in a manner similar to OPG.

EXAMPLE 2

The following describes the formation of osteoclast like cells from bone marrow cell cultures using a soluble RANKL in the form of soluble RANKL/leucine zipper fusion protein (RANKL LZ).

Using RANKL LZ at 1 µg/ml, osteoclasts were generated from murine bone marrow (BM) in the presence of CSF-1. These osteoclasts are formed by the fusion of macrophage-like cells and are characterized by their TRAP (tartrate-resistant acid phosphatase) positivity. No TRAP$^+$ cells were seen in cultures containing CSF-1 alone or in cultures containing CSF-1 and TRAIL LZ (a control for the soluble RANKL LZ). Even though human and monkey bone marrow contains more contaminating fibroblasts than murine bone marrow, osteoclasts were generated from murine and monkey bone marrow with the combination of CSF-1 and soluble RANKL LZ. In a dose-response study using murine bone marrow and suboptimal amounts of CSF-1 (40 ng/ml), the effects of soluble RANKL LZ plateaued at about 100 ng/ml.

The effect of soluble RANKL LZ on proliferation of cells was studied in the same cultures using Alamar Blue. After 5 days, the proliferative response was lower in cultures containing CSF-1 and RANKL LZ than in those containing CSF-1 alone. The supports the observation that soluble RANKL LZ is inducing osteoclast differentiation. When CSF-1 and RANKL LZ are washed out of murine BM cultures at day 7 or 8, cells do not survive if they are recultured in medium or in RANKL LZ alone. In contrast, cells do survive if recultured in CSF-1. When RANKL LZ was added to these cultures there was no added benefit. Thus, the combination of CSF-1 and RANKL are required for the generation of osteoclast. Additionally, once formed, CSF-1 is sufficient to maintain their survival in culture.

Finally, using human bone marrow, soluble anti-human RANK mAb and immobilized anti-human RANK mAb were compared to RANKL LZ for the generation of osteoclasts in the presence of CSF-1. Immobilized M331 and RANKL LZ were found to be equally effective for osteoclast generation while soluble M331 was superior to both immobilized antibody and RANKL LZ. This confirms that the osteoclast differentiating activity of RANKL is mediated through RANK rather than via an alternative receptor.

Since osteoclasts cannot readily be harvested and analyzed by flow cytometry, $^{125}$I-labeled calcitonin binding assays were used to identify osteoclasts (the calcitonin receptor is considered to be an osteoclast-specific marker). Osteoclasts generated from murine BM cultured with CSF-1 and RANKL LZ for 9 days showed binding of radiolabeled calcitonin confirming their osteoclast identity.

EXAMPLE 3

In order to determine RANKL expression by either of two different squamous cell carcinomas, standard Western blot and RT-PCR studies were performed on MH-85 and OKK cells. One of these carcinoma cells, the MH-85 cells, is associated with hypercalcemia.

The results confirmed that MH-85 and OKK squamous cells express RANKL. MH-85 cells, in addition to being linked with hypercalcemia in patients inflicted with this carcinoma, also express M-CSF (CSF-1). It was also determined that CSF-1 upregulates RANK expression on osteoclast precursors. The enhanced amount of CSF-1 in MH-85 type squamous cell cancer patients can lead to an upregulation of RANK and increased RANK interaction with RANKL. Signals transduced by RANK and RANKL interaction result in increased numbers of mature osteoclasts and bone breakdown. Since soluble forms of RANK can inhibit the RANK/RANKL interaction, administering a soluble form of RANK (e.g. the extracellular region of RANK fused to an Fc) to a squamous cell cancer patient provides relief from adverse effects of this cancer, including hypercalcemia.

We claim:

1. A method of inhibiting RANK-induced osteoclastogenesis in a patient in need thereof, comprising administering to the patient an antagonistic antibody that binds a RANKL polypeptide consisting of SEQ ID NO:8, wherein
the patient suffers from a condition selected from the group consisting of bone cancer, multiple myeloma, melanoma and breast cancer, and
the antibody is administered in an amount sufficient to inhibit RANK-induced osteoclastogenesis in the patient.

2. The method of claim 1, wherein the patient suffers from multiple myeloma.

3. The method of claim 1, wherein the patient suffers from breast cancer.

4. A method of inhibiting RANK-induced osteoclastogenesis in a patient in need thereof, the method comprising administering to the patient an antagonistic antibody that binds a RANKL polypeptide consisting of SEQ ID NO:8, wherein
the patient suffers from a condition selected from the group consisting of squamous cell carcinoma, lung cancer, prostate cancer, hematologic cancer, head and neck cancer and renal cancer, and
the antibody is administered in an amount sufficient to inhibit RANK-induced osteoclastogenesis in the patient.

5. The method of claim 4, wherein the patient suffers from prostate cancer.

6. The method of claim 4, wherein the patient suffers from lung cancer.

7. The method of claim 4, wherein the patient suffers from squamous cell carcinoma.

* * * * *

UNITED STATES PATENT AND TRADEMARK OFFICE
CERTIFICATE OF CORRECTION

PATENT NO. : 8,333,963 B2
APPLICATION NO. : 12/850368
DATED : December 18, 2012
INVENTOR(S) : Dirk M. Anderson It is certified that error appears in the above-identified patent and that said Letters Patent is hereby corrected as shown below:

Title page

Item (60): "Provisional application No. 60/110,836, filed on Dec. 3, 1998, provisional application No. 60/085,487, filed on May 14, 1998, provisional application No. 60/064,671, filed on Oct. 14, 1997, provisional application No. 60/077,181, filed on Mar. 7, 1997."

should read:

-- Provisional application No. 60/110,836, filed on Dec. 3, 1998, provisional application No. 60/085,487, filed on May 14, 1998, provisional application No. 60/064,671, filed on Oct. 14, 1997, provisional application No. 60/077,181, filed on Mar. 7, 1997, provisional application No. 60/059,978, filed on Dec. 23, 1996. --.

In the Specification

Col. 8, line 21: "Pagett's" should read -- Paget's --.

Signed and Sealed this
Twenty-second Day of April, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,333,963 B2
APPLICATION NO. : 12/850368
DATED : December 18, 2012
INVENTOR(S) : Anderson et al.

Page 1 of 1

It is certified that error appears in the above-identified patent and that said Letters Patent is hereby corrected as shown below:

Title Page

Item (60): "Continuation of application No. 12/137,397, filed on Jun. 11, 2008, now Pat. No. 7,790,684, and a continuation of application No. 09/705,985, and a continuation of application No. 11/881,911, filed on Jul. 30, 2007, which is a division of application No. 10/405,878, filed on Apr. 1, 2003, now Pat. No. 7,262,274, which is a continuation of application No. 09/871,291, filed on May 30, 2001, now Pat. No. 6,562,948, which is a division of application No. 09/577,800, filed on May 24, 2000, now Pat. No. 6,479,635, which is a continuation of application No. 09/466,496, filed on Dec. 17, 1999, now Pat. No. 6,528,482, which is a continuation of application No. 08/996,139, filed on Dec. 22, 1997, now Pat. No. 6,017,729."

should read:

-- Continuation of application No. 12/137,397, filed on Jun. 11, 2008, now Pat. No. 7,790,684, which is a continuation of application No. 09/705,985, filed on Nov. 3, 2000, now abandoned, which is a continuation of application No. PCT/US99/10588, filed on May 13, 1999, and application No. 12/137,397 is a continuation-in-part of application No. 11/881,911, filed on Jul. 30, 2007, now Pat No. 7,932,375, which is a division of application No. 10/405,878, filed on Apr. 1, 2003, now Pat. No. 7,262,274, which is a continuation of application No. 09/871,291, filed on May 30, 2001, now Pat. No. 6,562,948, which is a division of application No. 09/577,800, filed on May 24, 2000, now Pat. No. 6,479,635, which is a continuation of application No. 09/466,496, filed on Dec. 17, 1999, now Pat. No. 6,528,482, which is a continuation of application No. 08/996,139, filed on Dec. 22, 1997, now Pat. No. 6,017,729. --

Signed and Sealed this
First Day of July, 2014

Michelle K. Lee
*Deputy Director of the United States Patent and Trademark Office*